United States Patent
Greep et al.

(10) Patent No.: US 8,439,910 B2
(45) Date of Patent: May 14, 2013

(54) ELECTROSURGICAL ELECTRODE WITH ELECTRIC FIELD CONCENTRATING FLASH EDGE

(75) Inventors: Darcy W. Greep, Herriman, UT (US); Shawn K. Horner, Woods Cross, UT (US); Brian J. Walter, South Jordan, UT (US)

(73) Assignee: Megadyne Medical Products Inc., Draper, UT (US)

( * ) Notice: Subject to any disclaimer, the term of this patent is extended or adjusted under 35 U.S.C. 154(b) by 632 days.

(21) Appl. No.: 12/692,382

(22) Filed: Jan. 22, 2010

(65) Prior Publication Data

US 2011/0184410 A1 Jul. 28, 2011

(51) Int. Cl.
*A61B 18/14* (2006.01)

(52) U.S. Cl.
USPC .......................................................... 606/45

(58) Field of Classification Search .................... 606/27, 606/34, 41, 45
See application file for complete search history.

(56) References Cited

U.S. PATENT DOCUMENTS

| | | | |
|---|---|---|---|
| 4,161,950 A * | 7/1979 | Doss et al. ...................... 606/48 |
| 4,534,347 A | 8/1985 | Taylor |
| 4,674,498 A | 6/1987 | Stasz |
| 4,785,807 A | 11/1988 | Blanch |
| 4,848,337 A * | 7/1989 | Shaw et al. ...................... 606/28 |
| 5,380,320 A | 1/1995 | Morris |
| 5,643,256 A | 7/1997 | Urueta |
| 5,693,050 A | 12/1997 | Speiser |
| 5,697,926 A | 12/1997 | Weaver |
| 5,702,387 A | 12/1997 | Arts et al. |
| 5,759,183 A * | 6/1998 | VanDusseldorp ............... 606/46 |
| 5,766,153 A * | 6/1998 | Eggers et al. .................. 604/114 |
| 6,039,735 A | 3/2000 | Greep |
| 6,063,083 A | 5/2000 | Duong-Van |
| 6,066,137 A | 5/2000 | Greep |
| 6,287,305 B1 | 9/2001 | Heim et al. |
| 6,356,779 B1 * | 3/2002 | Katzenmaier et al. ........ 600/391 |
| 6,533,781 B2 | 3/2003 | Heim et al. |
| 6,589,237 B2 * | 7/2003 | Woloszko et al. ............. 606/41 |
| 6,766,202 B2 * | 7/2004 | Underwood et al. ........... 607/99 |
| 6,896,675 B2 * | 5/2005 | Leung et al. .................... 606/49 |
| 7,147,634 B2 | 12/2006 | Nesbitt |
| 7,150,747 B1 * | 12/2006 | McDonald et al. ............. 606/45 |
| 7,377,919 B2 | 5/2008 | Heim et al. |
| 2007/0005060 A1 | 1/2007 | Heim et al. |
| 2008/0319467 A1 | 12/2008 | Wenchell |

FOREIGN PATENT DOCUMENTS

WO  WO 2008/130525  10/2008

* cited by examiner

*Primary Examiner* — Michael Peffley
*Assistant Examiner* — Daniel Fowler
(74) *Attorney, Agent, or Firm* — Workman Nydegger

(57) ABSTRACT

An electrode tip for use in performing electro surgical operative procedures to concentrate electrical energy communicated to the patient tissue is disclosed. The electrode tip includes a main body that can receive electrical energy from an electrosurgical generator. The main body includes a working surface defining a flash edge. The working surface communicates the electrical energy to patient tissue during an operative procedure. The flash edge concentrates the electrical energy as it is communicated to the patient tissue. The concentration of the electrical energy from the flash edge reduces excessive tissue damage surrounding an incision site and improves the efficiency of the electrode tip.

25 Claims, 13 Drawing Sheets

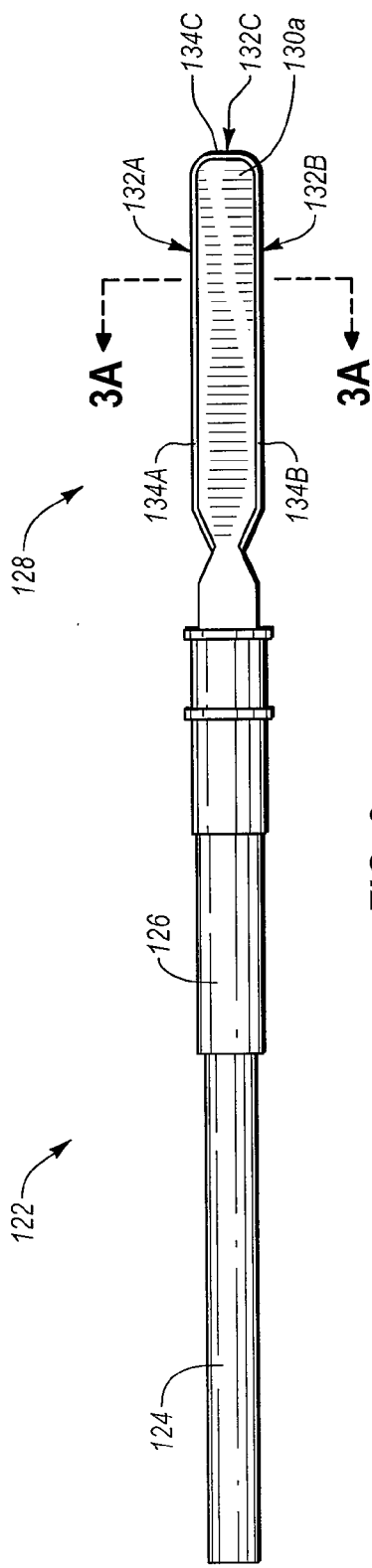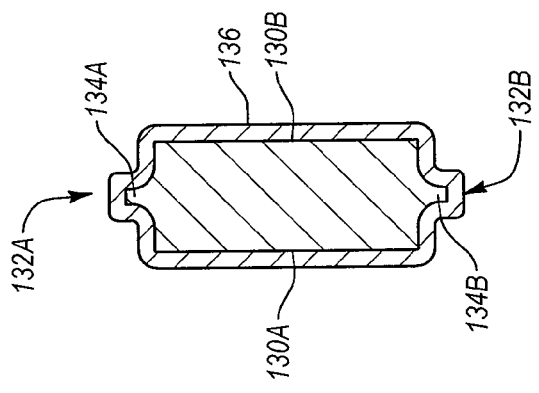
FIG. 3
FIG. 3A

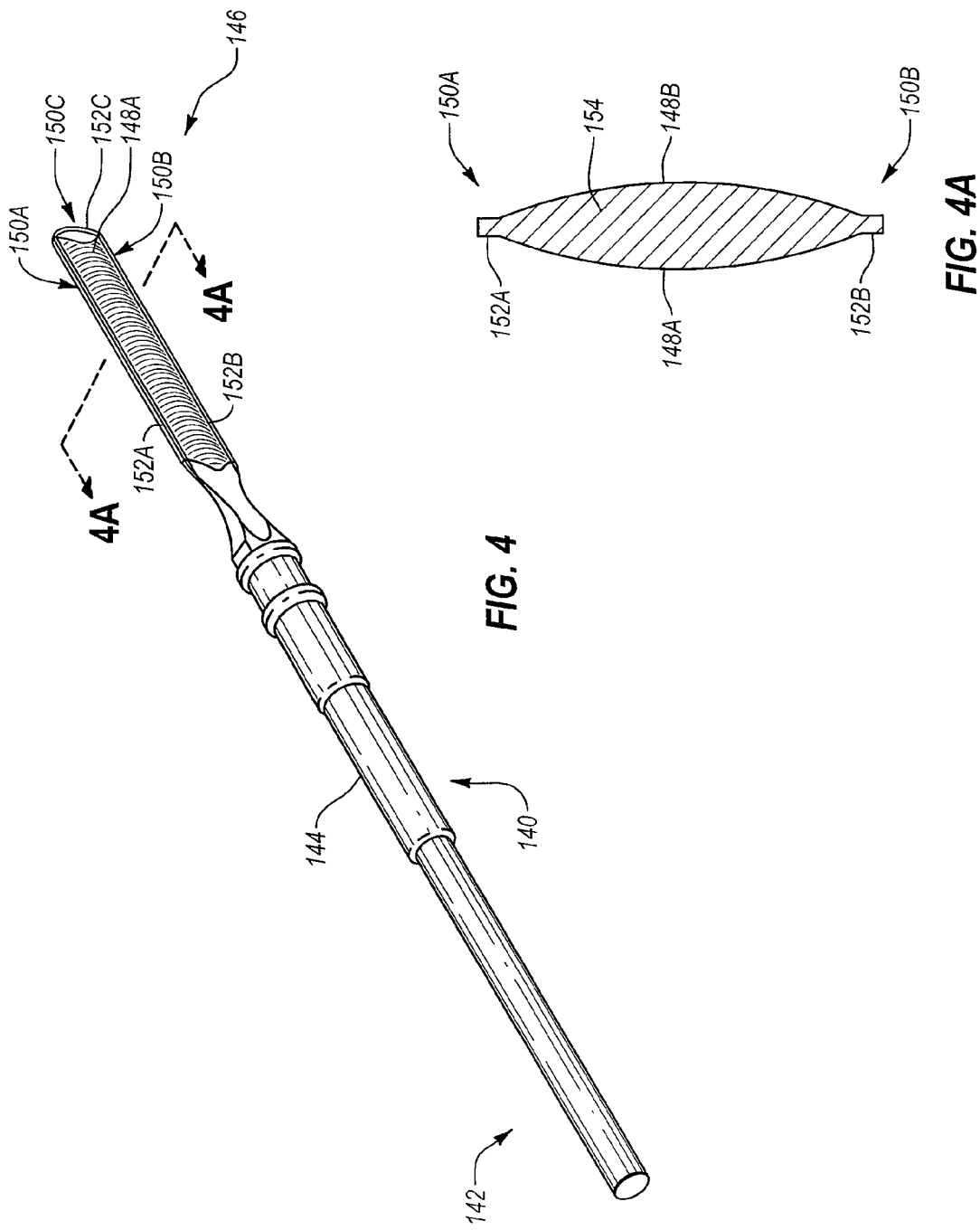

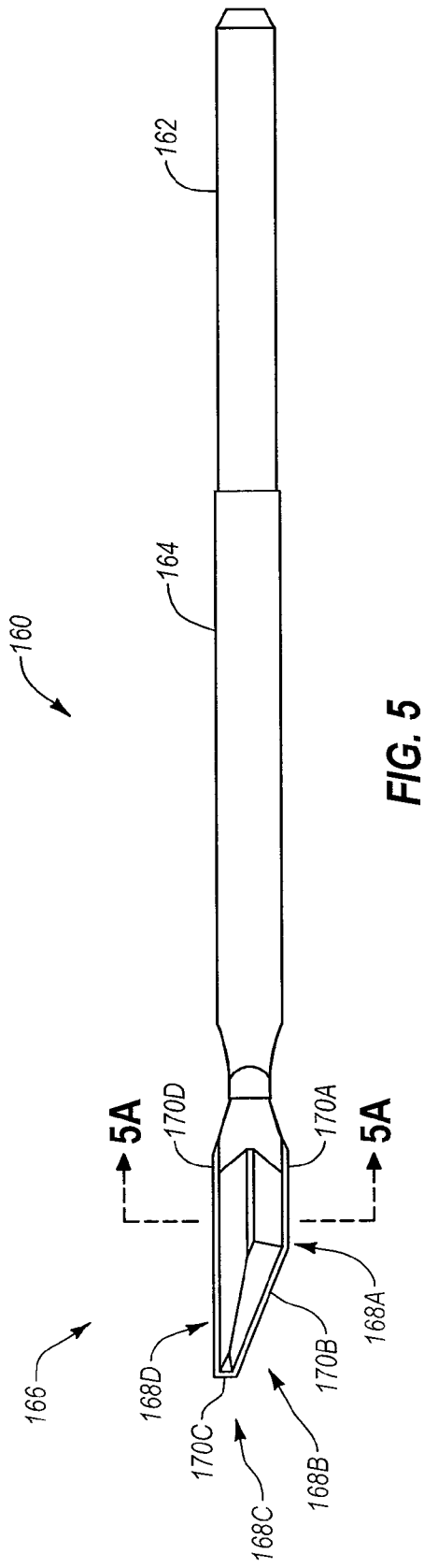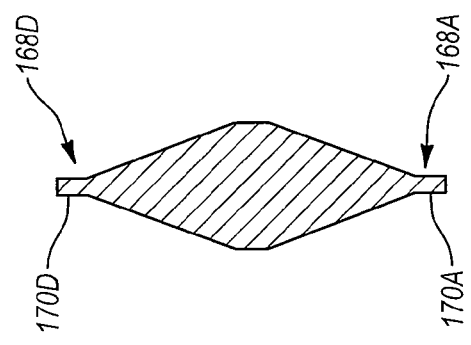
FIG. 5
FIG. 5A

ELECTROSURGICAL ELECTRODE WITH ELECTRIC FIELD CONCENTRATING FLASH EDGE

BACKGROUND OF THE INVENTION

1. The Field of the Invention

The present invention relates generally to electrosurgical devices. More specifically, the present invention relates to an electrosurgical electrode having a flash edge for concentrating an electric field generated during an electrosurgical procedure.

2. The Relevant Technology

In the area of electro surgery, medical procedures of cutting tissue and/or cauterizing leaking blood vessels are performed by utilizing radio frequency (RF) electrical energy. As is known to those skilled in the medical arts, electro surgery is widely used and offers many advantages including that of the use of a single surgical tool for both cutting and coagulation. The RF energy is produced by a wave generator and transmitted to a patient's tissue through a hand-held electrode that is operated by a surgeon. The hand-held electrode delivers an electrical discharge to cellular matter of the patient's body adjacent to the electrode to effect cutting.

In many electrosurgical systems, the electrode is an unsharpened blade which has been entirely coated with an insulating layer. With such an electrode, rather than using a mechanical action, cutting is performed by electrical energy capacitively transferred through the insulating layer to the tissue which is to be cut. In such electro surgery, "cutting" is accomplished when energy transfer is sufficient to cause water in tissue cells to boil, thus rupturing the cell membranes by internal rather than external forces. Relatively high energy levels have been required to effect such electrosurgical cutting.

The concentration of the RF energy discharge affects both the efficiency with which the electrode is able to cut tissue and the extent of thermal damage to adjacent tissues. With a standard electrode geometry, the RF energy tends to be distributed over a relatively large area of the active electrode surface. This broad distribution of RF discharge requires greater energy output to achieve the desired electrosurgical effect, which increases the likelihood of extraneous charge loss into surrounding tissue, resulting in unwanted and excessive thermal damage to surrounding tissue.

While standard electrode geometries have found widespread acceptance in the field of electro surgery, there has been a continuing need for further improvement in electro surgery to effect a reduction in thermal necrosis, thereby decreasing post-operative complication, reducing eschar production, reducing incidence of heat damage to tissue away from the cutting site, and increasing the precision and speed of cutting. Therefore, it would be an advantage to have an electrode that increases the concentration of the RF energy discharge, while at the same time limiting unwanted tissue damage. The subject matter claimed herein, however, is not limited to embodiments that solve any disadvantages or that operate only in environments such as those described above. Rather, this background is only provided to illustrate one exemplary technology area where some embodiments described herein may be practiced.

BRIEF SUMMARY OF THE INVENTION

The present invention relates generally to electrosurgical devices. More specifically, the present invention relates to an electrosurgical electrode having a flash edge disposed about at least a portion thereof. The inclusion of a flash edge on the electrode introduces and/or enhances properties, characteristics, and/or attributes of the electrode. For instance, the flash edge of an electrode tip can be configured to produce significantly improved performance in cutting efficiency and post-operative recovery, while dramatically reducing unwanted tissue damage surrounding an incision. The flash edge is adapted to concentrate electrical energy transferred from the electrode tip to the patient's tissue during an electrosurgical procedure. The concentrated electrical energy reduces the amount of extraneous charge loss into surrounding tissue, thereby reducing the amount of necrotic damage in the tissue surrounding the incision site. Additionally, the manufacturing process for forming an electrode tip with a flash edge is relatively simple and it leads to more consistency in desired dimensions and quality in the electrode tips. The consistency in the desired dimensions results in improved performance when the electrode tip is used to perform electrosurgery. Furthermore, the flash edge makes the electrode more resilient to the reduction of the desired edge dimension during processing of the electrode, such as tumbling, polishing, sanding, and the like. Additionally, when the electrode tip is coated, the inclusion of the flash edge leads to improved coating retention on the electrode tip.

Implementation of an exemplary embodiment of the present invention takes place in association with a surface, such as at least a portion of the surface of an electrosurgical electrode tip that may be used to cut tissue and/or cauterize blood vessels of a patient during an electrosurgical operation. The surface includes a relatively narrow ridge that is be used to effect electrosurgical cutting. The narrow ridge, or flash edge, achieves an important concentration of electrosurgical energy to permit more rapid and effective cutting of tissue. Additionally, because cutting is effectuated as a result of the concentration of electrosurgical energy, rather than the sharpness of a normal mechanical scalpel, an electrode according to the present invention is safer to handle than a scalpel because the working surface of the electrode tip is not required to be as sharp as a scalpel, thus reducing the risk of a mechanical cut to a physician or other operating room personnel while handling the electrode. The concentration of electric field and energy transfer due to the sharpened working edge of the electrode tip provides a marked improvement in charge concentration and tissue severance and results in reduced thermal necrosis, more rapid cutting, and reduced eschar production.

Exemplary embodiments of the present invention provide an electrode tip having a flash edge that can be partially or completely coated. The electrode tip coating can comprise a non-stick coating, such as polytetrafluoroethylene ("PTFE") or TEFLON®, or a hybrid material that can include a combination of at least one of an organic material and an inorganic material to provide various desirable properties to the electrode, such as high temperature stability, flexibility, and a low temperature application.

It has been found that such electrode tips present a marked improvement in performance over the proposals heretofore made by further concentrating electrosurgical energy, thus permitting more rapid and effective cutting at lower RF energy levels while resulting in reduced thermal necrosis, more rapid cutting, and reduced eschar production. The principles hereof may be applicable to blades, points or needles, forceps, modified ball electrodes, L-hooks, L-wires, J-hooks, and similar constructions.

In one exemplary implementation of the present invention, an electrode tip includes a connection end and a main body. The connection end is electrically connected to an electrosurgical generator to facilitate communication of electrical energy from the electrosurgical generator to the electrode tip. The main body is formed of a conductive material and is operatively associated with the connection end. The main body has two opposing major surfaces and a working surface. The two opposing major surfaces can be generally parallel to one another, or they can be rounded or taper closer together as they approach the working surface.

The working surface includes a flash edge that communicates the electrical energy from the main body to patient tissue during the performance of an electrosurgical operative procedure. The flash edge can have two opposing side surfaces and a face surface. The two opposing side surfaces extend from the main body. In one exemplary embodiment, the two opposing side surfaces extend from the two opposing major surfaces of the main body at an angle of between about 90° and less than about 180°. The two opposing side surfaces of the flash edge are spaced apart a distance to concentrate the electrical energy communicated to the patient tissue. For example, the two opposing side surfaces can be spaced apart a distance of between about 0.0125 mm and about 0.125 mm, more preferably between about, 0.0254 mm and 0.1016 mm, and more preferably about 0.0762 mm. The flash edge can extend from the main body by a distance of between about 0.0125 mm and about 6.5 mm. The flash edge can be sized such that at least a portion of the flash edge can act as a sacrificial element. That is, a portion of the flash edge can be removed without significantly compromising the electrical energy concentrating capabilities of the flash edge. All or a part of the main body and/or working surface can have a coating applied thereto. The coating can be a non-stick and/or insulative material.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 3 is a side view of an electrode tip embodying principles according to the invention;

FIG. 3A is a cross-sectional view of the electrode tip of FIG. 3 and depicting working surfaces of the electrode tip that include flash edges extending therefrom;

FIG. 4 is a perspective view of an electrode tip having tapered sides and flash edges extending therefrom;

FIG. 4A is a cross-sectional view of the electrode tip of FIG. 4 and depicting the tapered sides and the flash edges extending therefrom;

FIG. 5 is a perspective view of a scalpel-type electrode tip having multiple working surfaces and flash edges extending therefrom;

FIG. 5A is a cross-sectional view of the electrode tip of FIG. 5 and depicting two working surfaces of the electrode tip with flash edges extending therefrom;

DETAILED DESCRIPTION OF THE PREFERRED EMBODIMENTS

The present invention relates generally to electrosurgical devices. More specifically, the present invention relates to an electrosurgical electrode having a flash edge disposed about at least a portion thereof for concentrating an electric field generated during an electrosurgical procedure. As discussed in greater detail below, the inclusion of a flash edge on the electrode introduces and/or enhances properties, characteristics, and/or attributes of the electrode. Briefly, for instance, the manufacturing process of an electrode tip with a flash edge is relatively simple and it leads to more consistency in desired dimensions and quality in the electrode tips. The consistency in the desired dimensions results in improved performance when the electrode is used to perform electrosurgery. Furthermore, the flash edge makes the electrode more resilient to the reduction of the desired edge dimension during processing of the electrode, such as tumbling, polishing, sanding, and the like. Additionally, when the electrode is coated, the inclusion of the flash edge leads to improved coating retention on the electrode.

Reference will now be made to the drawings to describe various aspects of exemplary embodiments of the invention. It is understood that the drawings are diagrammatic and schematic representations of such exemplary embodiments, and are not limiting of the present invention, nor are any particular elements to be considered essential for all embodiments or that elements be assembled or manufactured in any particular order or manner. No inference should therefore be drawn from the drawings as to the necessity of any element. In the following description, numerous specific details are set forth in order to provide a thorough understanding of the present invention. It will be obvious to one of ordinary skill in the art, however, that the present invention may be practiced without these specific details. In other cases, well known aspects of electrosurgical systems, devices, and methods, and general manufacturing techniques are not described in detail herein in order to avoid unnecessarily obscuring the novel aspects of the present invention.

FIGS. 1-17A and the following discussion are intended to provide a brief general description of exemplary devices in which embodiments of the invention may be implemented. While electrodes for electrosurgical systems are described below, these are but a few examples, and embodiments of the invention may be implemented with other types of electrical systems. Accordingly, throughout the specification and claims, the phrases "electrosurgical electrode," "electrode," "electrode blade," "electrode tip," and the like are intended to apply broadly to any type of item that can be used to concentrate an electric field as described herein.

Figure 1:
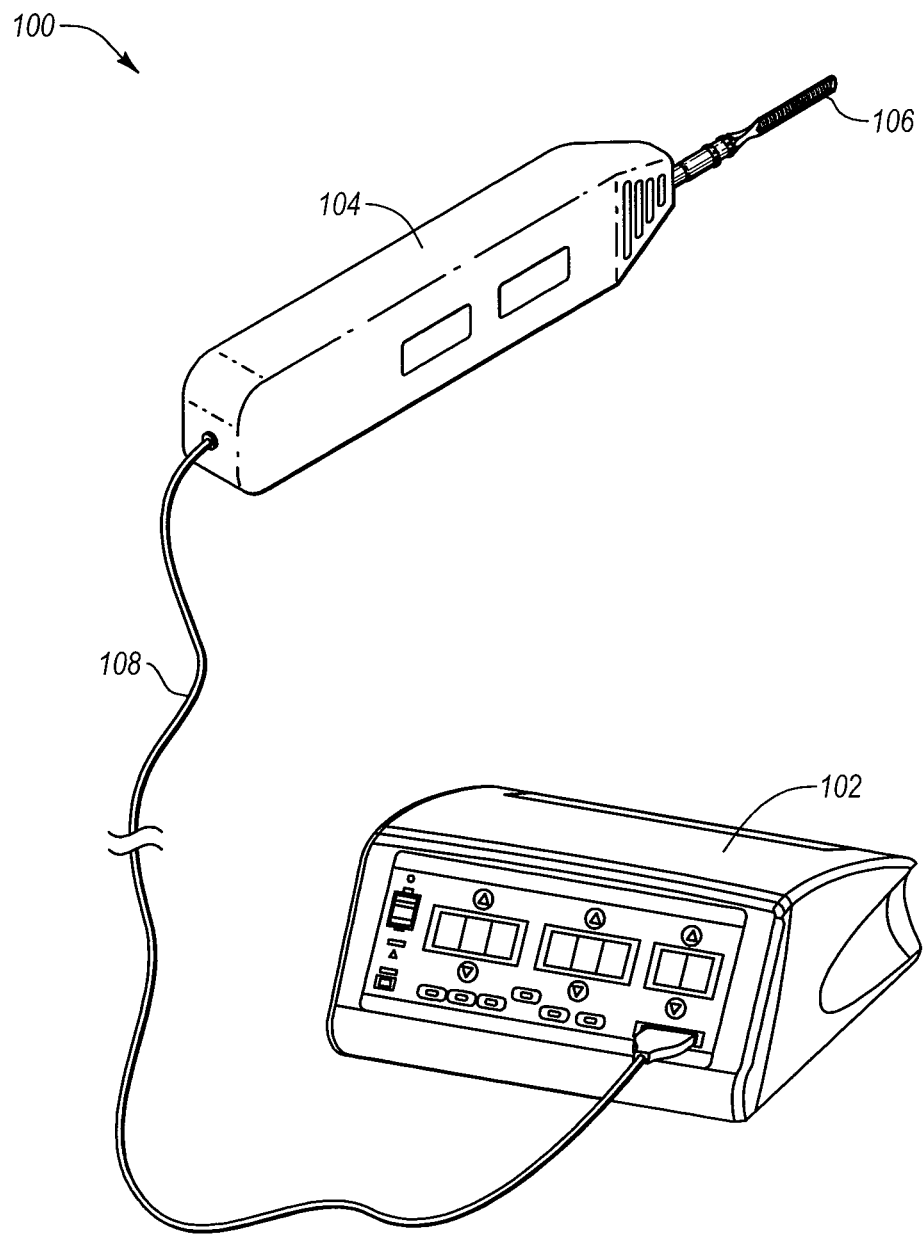
FIG. 1 illustrates an exemplary electrosurgical system according to the present invention.

FIG. 1 and the corresponding discussion are intended to provide a brief, general description of an operating system in which one embodiment of the invention may be implemented. Although not required, the invention will be described in the general context of providing specific properties, attributes, and/or characteristics to an electrosurgical electrode and a working surface thereof in order to improve the quality of electrosurgical operations and limit damage to the tissue of a patient resulting from electrosurgery. Those skilled in the art, however, will appreciate that embodiments of the present invention may be practiced in association with a variety of different surfaces in order to provide desirable properties, attributes, and/or characteristics during electrosurgery.

Referring to FIG. 1, an exemplary system is illustrated that can include the features of the present invention. In FIG. 1, electrosurgical system 100 is illustrated, which includes a wave generator 102, a hand-held electrode 104, and an electrode tip 106. Generator 102, in a preferred embodiment, is an RF wave generator. A surgeon may use electrosurgical system 100 during surgical procedures to cut tissue and/or cauterize blood vessels of a patient's body.

In electrosurgery, radio frequency (RF) electrical energy is produced by a wave generator, such as wave generator 102, and is introduced to a patient's body by a hand-held electrode, such as electrode 104, which is electrically coupled to wave generator 102 and includes electrode tip 106. Wave Generator 102 can include a high-frequency oscillator and amplifiers to generate an RF electrical energy wave that can be used to cut tissue and/or cauterize blood vessels during electrosurgery. The RF electrical energy wave powers electrode 104 and is transmitted from wave generator 102 to electrode 104 via cord 108. An electrical discharge is delivered from electrode tip 106 to the patient in order to cause the heating of cellular matter of the patient that is in close contact to electrode tip 106. The heating takes place at an appropriately high temperature to allow electrode 104 to be used to perform electrosurgery. A grounding electrode (not shown) provides a return electrical path to wave generator 102 for any excess charge that is dissipated into surrounding tissue of the patient's body.

During electrosurgery, electrode 104 may be used to independently or concurrently cut and cauterize. A constant sinusoidal wave supplied by wave generator 102 and transmitted to electrode 104 allows electrode tip 106 to cut through tissue of the patient's body. Alternatively, a damped wave supplied by wave generator 102 and transmitted to electrode 104 allows electrode tip 106 to cauterize leaking blood vessels and/or tissues. A combination of the constant sinusoidal wave and the damped wave can be supplied by wave generator 102 to electrode 104 for allowing electrode tip 106 to concurrently cut and cauterize, thereby minimizing tissue trauma and blood loss during the surgical procedure.

Figures 2, 2A:
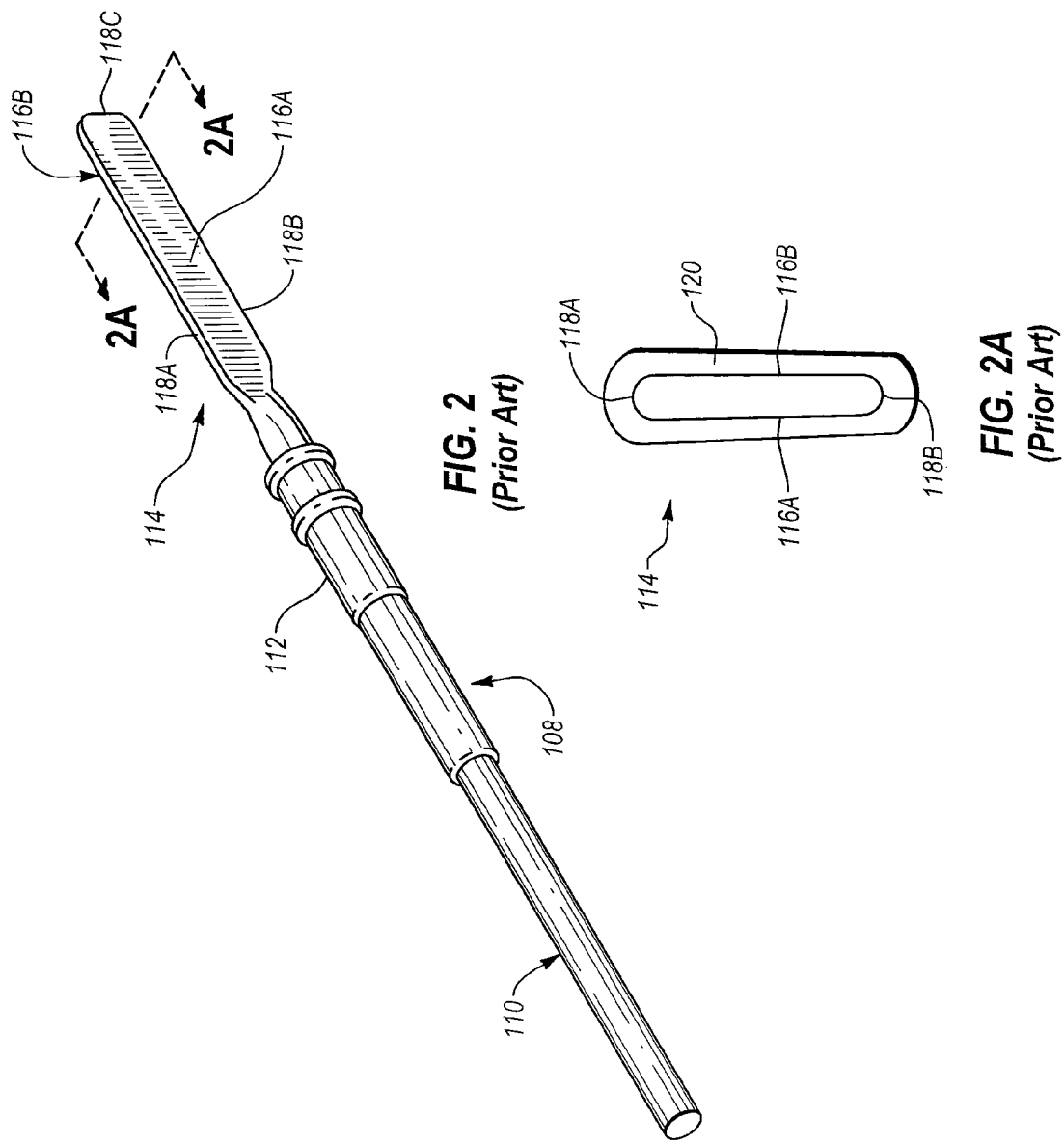
FIG. 2 is a perspective view of an electrosurgical electrode tip according to the prior art.
FIG. 2A is a cross-sectional view of the electrode tip of FIG. 2.

With attention to FIGS. 2 and 2A, there is illustrated an electrosurgical electrode tip 108 commonly used to perform electrosurgical procedures. As seen in FIG. 2, electrode tip 108 includes a connection end 110 fitted with a sleeve fitting 112 positioned around the electrode shank to provide protection and to facilitate coupling of electrode tip 108 to a hand-held electrode, such as electrode 104. Electrical discharge is delivered to the patient's body from working end 114, which is in a standard blade-type electrode configuration. That is, working end 114 has two flat and substantially parallel major surfaces 116A, 116B and two generally parallel working surfaces 118A, 118B. The end of electrode tip 108 can also be formed into a working surface 118C. Electrode tip 108 can create an incision similar to a traditional scalpel. Rather than employing a mechanical action for cutting through tissue as is done with a scalpel, however, the electrical discharge allows working end 114 to slide through the tissue as the tissue is being superheated to an appropriate temperature to perform the electrosurgical procedure. As illustrated in FIG. 2A, a coating 120 of non-stick and/or insulating material covers the surface of electrode tip 108 and serves to eliminate or reduce the clinging of charred tissue to electrode tip 108, and or facilitate capacitive coupling of electrode tip 108 to the patient's tissue.

Turning now to FIGS. 3-11, there is illustrated an exemplary assortment of interchangeable electrode tips that include the beneficial features of the present invention to facilitate the acts of cutting tissue and/or cauterizing blood vessels. The illustrated assortment of electrode tips include a standard-type electrode tip, a shaped electrode tip with tapered working surfaces, a scalpel-type electrode tip, a needle electrode, a loop electrode, a modified ball electrode, and various laparoscopic electrodes for use with a conventional electrosurgical holder, such as hand-held electrode 104 seen in FIG. 1. Each of the interchangeable electrode tips has a connection end that can be coupled to the hand-held electrode 104 to allow RF electrical energy generated by wave generator 102 to be transmitted through hand-held electrode 104 to the electrode tip. The lengths of the connection ends of the various electrode tips can vary depending on the specific type of electrode tip and/or the type of procedure for which the electrode tip is used. For instance, the lengths of the connection ends may range from about 6.35 cm to about 48 cm. In some embodiments, the lengths of the connection ends are about 6.35 cm, 6.9 cm, 10.16 cm, 15.24 cm, 33 cm, 45 cm, and 48 cm. It will be appreciated that the lengths of the connection ends can be any suitable lengths and the above-mentioned lengths are only exemplary and not intended to limit the scope of the present invention.

Each of the illustrated electrode tips includes a sleeve fitting positioned around the electrode shank to provide protection and to facilitate coupling of the electrode tip to a hand-held electrode, such as electrode 104. Each electrode tip also includes a working end that applies the electrical discharge to the patient's body. All or a portion of the working ends can have a coating of non-stick that serves to eliminate or reduce the clinging of charred tissue to the electrode tip. The electrode tips can also have an insulator that covers at least a portion of the working end. For example, an insulative material can be applied to a portion of the working end of the electrode tip in order to provide an insulative barrier between a portion of the working end and a patient's tissue. In one embodiment, the insulative material is applied around the working end of the electrode tip, leaving only a small part of the electrode tip exposed for use during electrosurgery. For example, the insulative material may cover the entire working end except for a flash edge. The exposed flash edge can then be used to perform electrosurgery without electrical discharge between the rest of the working end and the patient's tissue.

The working ends of the illustrated electrodes can be configured to provide great versatility in cutting and/or cauterizing tissue and/or blood vessels in a variety of different surgical procedures. Furthermore, the electrode tips can be configured to produce significantly improved performance in cutting efficiency and post-operative recovery, while dramatically reducing unwanted tissue damage surrounding an incision. For instance, each of the electrode tips illustrated in FIGS. 3-11 includes or is formed with one or more "flash edges." As described in greater detail below, the flash edges concentrate the electrical energy transferred from the electrode tip to the patient's tissue. The concentrated electrical energy reduces the amount of extraneous charge loss into surrounding tissue, thereby reducing the amount of necrotic damage in the tissue surrounding the incision site.

With specific reference to FIGS. 3-11, various aspects of each of the illustrated electrode tips will now be described. As noted above and identified below in connection with the embodiments illustrated in FIGS. 3-11, each of the electrode tips can include one or more flash edges. While these flash edges are identified in connection with the discussion of FIGS. 3-11, a more detailed discussion of the features, advantages, and parameters applicable to each of these flash edges, regardless of the overall configuration of the particular electrode tip, will follow the discussion of the individual electrode tip embodiments.

FIGS. 3 and 3A illustrate electrode tip 122, which is an electrode tip that may be used in general surgery for cutting tissue and/or for cauterizing blood vessels. Electrode tip 122 includes connection end 124 fitted with a sleeve fitting 126 positioned around the electrode shank to provide protection and to facilitate coupling of electrode tip 122 to hand-held electrode 104. Electrical discharge is delivered to the patient's body from working end 128, which is, generally, in a standard blade-type electrode tip configuration. That is, working end 128 has two substantially parallel major surfaces 130A, 130B and two generally parallel working surfaces 132A, 132B. The end of electrode tip 122 can also be formed into a working surface 132C. Like a standard blade-type electrode, electrode tip 122 can create an incision similar to a traditional scalpel. Rather than employing a mechanical action for cutting through tissue as is done with a scalpel, however, the electrical discharge allows working end 128 to slide through the tissue as the tissue is being superheated to an appropriate temperature to perform the electrosurgical procedure.

Unlike a standard blade-type electrode, however, one or more of working surfaces 132A, 132B, 132C of electrode tip 122 are not flat and generally squared off relative to major surfaces 130A, 130B. Rather, one or more of working surfaces 132A, 132B, 132C comprises a flash edge. That is, at least one of working surfaces 132A, 132B, 132C includes a raised or flash edge, such as flash edges 134A, 134B, 134C shown in FIGS. 3 and 3A. As discussed in greater detail below, flash edges comprise a relatively thin ridge that extends along at least a portion of a working surface to provide and/or enhance the characteristics, features, and/or attributes of the electrode tip. In addition to the flash edge(s), electrode tip 122 can also include a non-stick coating 136 that surrounds at least a portion of working end 128.

While electrode tip 122 is illustrated with a flash edge extending around nearly the entirety of electrode tip 122, it will be appreciated that a flash edge may be included along a portion or the entirety of any working surface of electrode tip 122. Similarly, while the flash edges 134A, 134B, 134C are illustrated as extending from the middle of the working surface 132A, 132B, 132C, respectively, or being centered between the major surfaces 130A, 130B such that the vertical surfaces of the flash edges 134A, 134B, 134C are offset from the major surfaces 130A, BOB, the flash edges 134A, 134B, 134C can extend from other locations on the working surfaces 132A, 132B. By way of non-limiting example, flash edge 134A may be located to the left of the illustrated positioned. For instance, the left vertical surface of flash edge 134A may be aligned with major surface 130A, while the left vertical surface of flash edge 134A is further offset from major surface 13OB.

FIGS. 4 and 4A depict an electrode tip similar to that shown in FIG. 3. Thus, in FIGS. 4 and 4A there is seen an electrosurgical electrode tip 140 having a connection end 142 fitted with a sleeve fitting 144 positioned around the electrode shank to provide protection and to facilitate holding of electrode tip 140 by a conventional electrode, such as electrode 104 as seen in FIG. 1. Electrode 140 also includes a working end 146 that is formed with a shaped or sharpened geometry and includes flash edges.

As seen in FIGS. 4 and 4A, the illustrated embodiment features a cross sectional geometry which includes two opposing major surfaces 148A, 148B and two generally parallel working surface 150A, 150B. Working end 146 can also include a working surface 150C at the end thereof. In the illustrated embodiment, working surfaces 150A, 150B, 150C have flash edges 152A, 152B, 152C, respectively, extending therefrom. Working surface 150A, 150B, 150C can be used to cut tissue and/or cauterize blood vessels during an electrosurgical procedure.

FIG. 4A is a sectional view of working end 146 of electrode tip 140 taken along the section lines 4A—4A of FIG. 4. There, it will be seen is electrically conductive main body 154 which may be of any suitable material such as, preferably, surgical grade stainless steel. Major surfaces 148A, 148B of body 154 have been tapered to form working surfaces 150A, 150B. Extending from working surfaces 150A, 150B are flash edges 152A, 152B, each of which, as described in more detail below, concentrates or focuses the electric field created when electrical potential is applied to the electrode tip, thus increasing the concentration of transferred electrical energy and correspondingly improving efficiency with which the implement achieves a cutting action, e.g., severing tissue, and reducing the amount of extraneous charge loss in tissue which is not in close proximity to the working surface. While not illustrated, working end 146 of electrode tip 140 can also include a coating that surrounds at least a portion of working end 146.

Turning now to FIGS. 5 and 5A, there is seen an electrode tip 160 which can also be used in general surgery for cutting tissue and/or for cauterizing blood vessels. Electrode tip 160 includes connection end 162 and sleeve fitting 164 positioned around the electrode shank to provide protection and to facilitate holding of electrode tip 160 by a conventional electrosurgical holder as seen in FIG. 1. Electrode tip 160 also includes working end 166. Working end 166 is in a scalpel-like blade configuration that has a profile that resembles a mechanical scalpel. Similar to electrode tip 140 illustrated in FIGS. 4 and 4A, working end 166 of electrode tip 160 includes multiple shaped or tapered working surfaces 168A, 168B, 168C, 168D. Working surfaces 168A, 168B, 168C, 168D have similar cross-sectional shapes as surfaces 150A, 150B, and 150C described above. More specifically, working surfaces 168A, 168B, 168C, 168D are shaped or tapered and include flash edges 170A, 170B, 170C, 170D, respectively, extending therefrom, which concentrate or focus the electric field created when electrical potential is applied to electrode tip 160. As noted, the details of the shaping or tapering of the working surfaces along with the flash edges will be discussed in more detail below.

Because cutting with working surfaces 132A, 132B, 132C, 150A, 150B, 150C, 168A, 168B, 168C, and 168D is effectuated as a result of the concentration of electrosurgical energy rather than the sharpness of a normal mechanical scalpel, an electrode according to the present invention is safer to handle than a scalpel because the working surfaces of the electrode are not required to be as sharp as a mechanical scalpel, thus reducing the risk of a mechanical cut to a physician or other operating room personnel while handling the electrode.

As can be seen in FIG. 5, working surfaces 168A, 168B, 168C, 168D are formed with differing lengths and can be angled relative to one another. The differing lengths and orientation of working surfaces 168A, 168B, 168C, 168D in the illustrated embodiment gives working end 166 a profile resembling a mechanical scalpel. The scalpel-like profile allows for great versatility when using electrode tip 160. The differing lengths and orientation of the working surfaces can allow a surgeon to make many different types of incisions and cauterize large or small areas with a single electrode tip. For instance, the inclusion of a shorter working surface and a longer working surface in a single electrode enables a surgeon to use the same electrode to create different types of incisions during a single procedure without having to change electrodes. Rather, the surgeon can simply rotate the electrode to utilize the desired working surface.

By way of non-limiting example, working surface 168A can be sized to make relatively shallow and/or delicate incisions in a patient's skin. The length of working surface 168A can also help prevent a surgeon from inadvertently cutting too deep. Once the shallow incision is made, the surgeon can then rotate electrode tip 160 by 180° and use working surface 168D to make a deeper incision, such as in a subcutaneous layer. In one embodiment, working surface 168A is about 3 mm long and working surface 168D is about 8 mm long. In another embodiment, working surface 168A is about 4 mm long and working surface 168D is about 11 mm long. Other lengths and combinations can also be used for the different working surfaces. Additionally, working surface 168C can be sized to enable a surgeon to cut and/or cauterize a very small area without having to replace electrode tip 160 with a needle electrode, for example. In one embodiment, working surface 168C is about 0.5 mm long. Thus, the shape and size of working surface 168C can provide the ability to perform nearly pinpoint incisions and/or coagulation. It will be appreciated that electrode tip 160 can be formed with fewer or more working surfaces 168.

Figure 6:
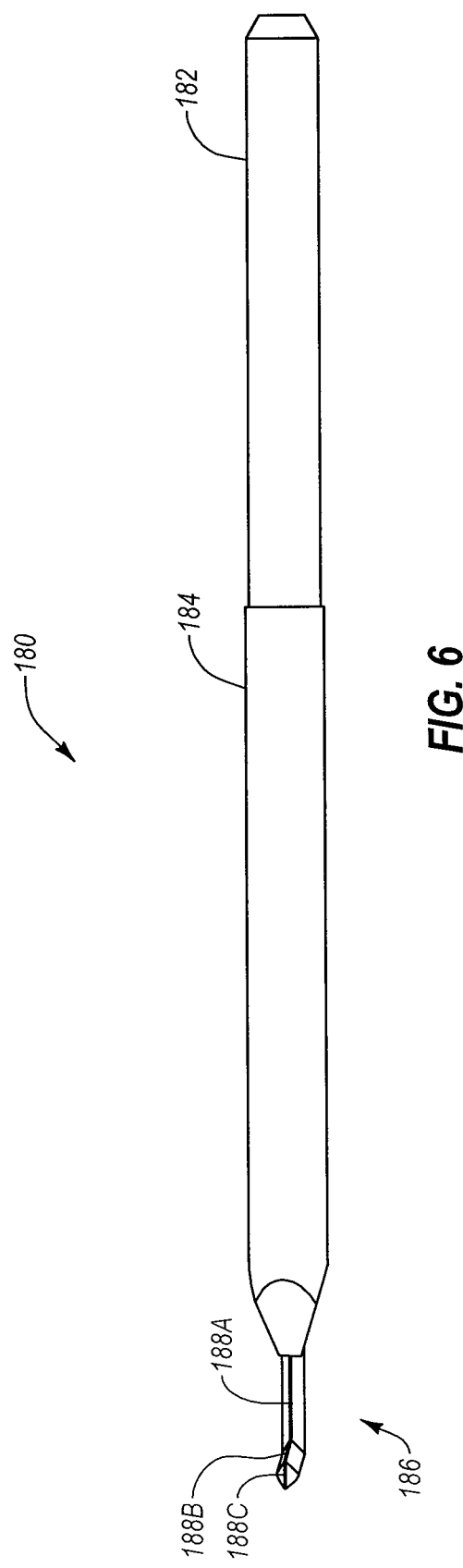
FIG. 6 is a perspective view of an L-hook electrode tip configured to have one or more flash edges according to an exemplary embodiment of the present invention.

FIG. 6 illustrates electrode tip 180, which is an electrode tip that may facilitate a surgeon in reducing extraneous tissue damage by allowing individual tissues or blood vessels to be isolated and independently cut and/or cauterized. Electrode tip 180 includes connection end 182 and a sleeve fitting 184. Electrode tip 180 also includes working end 186 that has an L-hook configuration. In the illustrated embodiment, working end 186 has three working surfaces 188A, 188B, 188C, each of which is shaped or tapered as described herein. In addition, one or more of working surfaces 188A, 188B, 188C includes a flash edge (not shown) similar to those described above. It will be appreciated that electrode tip 180 can be formed with fewer or more working surfaces 188.

Figure 7:
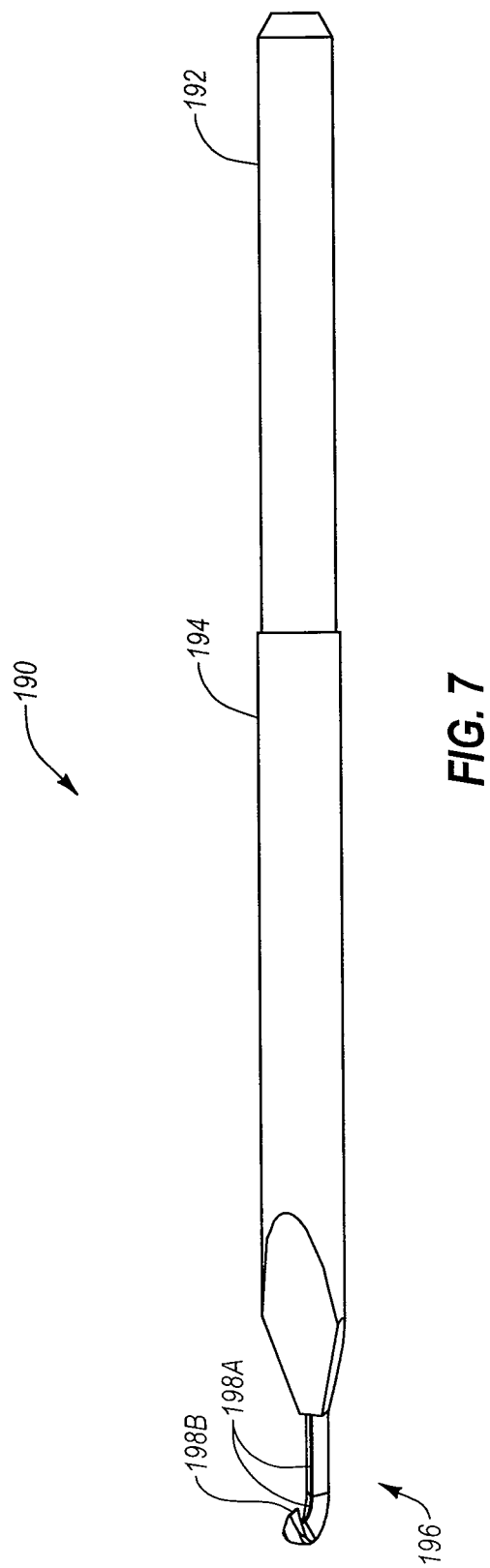
FIG. 7 is a perspective view of a J-hook electrode tip configured to have one or more flash edges according to an exemplary embodiment of the present invention.

FIG. 7 illustrates electrode tip 190 that is similar to electrode tip 180. Electrode tip 190 includes connection end 192, sleeve fitting 194, and working end 196. Working end 196 is in a J-hook configuration and has two working surfaces 198A, 198B, each of which is shaped or tapered as described herein. At least one of working surfaces 198A, 198B includes a flash edge (not shown) as described herein. Electrode tip 190 can be formed with fewer or more working surfaces 198.

Figure 8:
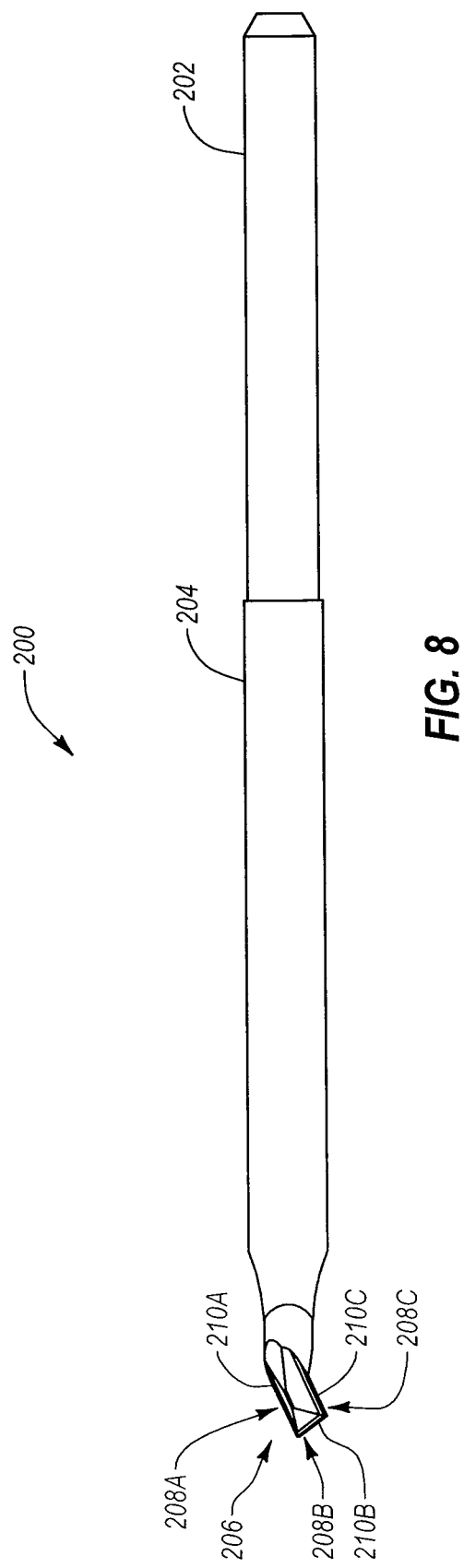
FIG. 8 is a perspective view of another electrode tip having multiple working surfaces with flash edges according to exemplary embodiments of the present invention.

FIG. 8 illustrates electrode tip 200, which includes connection end 202, sleeve fitting 204, and working end 206. Working end 206 has three working surfaces 208A, 208B, 208C, each of which is shaped or tapered as described herein. Electrode tip 200 can be formed with fewer or more working surfaces 208. As with the other electrode tips, one or more of the working surfaces includes a flash edge extending therefrom. In the illustrated embodiment, working surfaces 208A, 208B, 208C include flash edges 210A, 210B, 210C, respectively.

Figure 9:
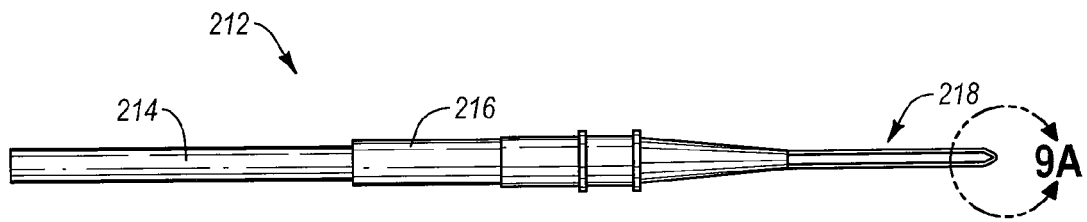
FIG. 9 illustrates an exemplary needle-type electrode tip having a flash edge extending along a portion thereof.
Figure 9A:
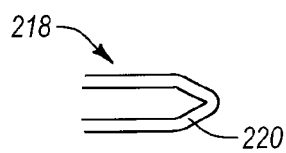
FIG. 9A illustrates a close-up view of the working end and flash edge of the electrode tip of FIG. 9.

FIGS. 9 and 9A illustrate electrode tip 212, which is an electrode tip that may be used for cutting tissue and cauterizing leaking blood vessels in particularly dense areas of a patient's body, such as those experienced in cerebral operations. Electrode tip 212 includes connection end 214, sleeve fitting 216, and working end 218. Working end 218 is in a needle-like configuration that comes to a point to allow for very accurate surgical procedures in dense areas of the patient's body. As best seen in FIG. 9A, the tip and/or sides of working end 218 can be formed with flash edges 220 as described herein. For instance, the shaft of the needle may have one or more flash edges 220 extending along at least a portion of the length thereof. The "point" of the needle may also include a flash edge 220 (i.e., a portion that extends from the end of the needle as illustrated). Through the use of electrode tip 212, delicate cerebral tissues can be accurately removed with virtually no damage to any surrounding membranes and with minimal bleeding and/or swelling resulting from the procedure.

Figure 10:
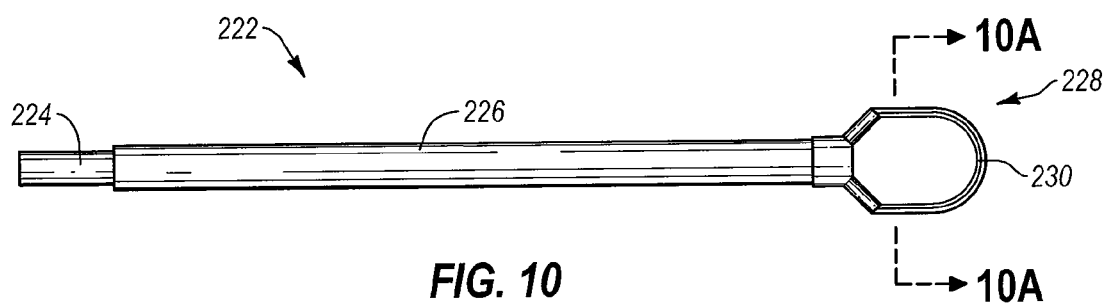
FIG. 10 illustrates a loop-type electrode tip for use in removing large sections of tissue, the electrode tip having a flash edge extending along the loop.
Figure 10A:

FIGS. 10 and 10A illustrate electrode tip 222, which is an electrode tip that may be used for the removal of large sections of tissue, as in, for example, prostate and tumor excision. Electrode tip 222 includes connection end 224, sleeve fitting 226, and working end 228. Connection end 224 is coupled to the hand-held electrode while working end 228 is used to delivered electrical energy to the patient's body. Working end 228 is in a loop-like configuration. As best seen in FIG. 10A, the loop of working end 228 can be formed with a flash edge 230. In the illustrated embodiment, flash edge 230 is disposed on the inside of the loop so as to provide the desired performance characteristics when the loop is pulled through tissue. In alternative embodiments, flash edge 230 can also be disposed on one or both sides of the loop to provide similar functionality. In yet other exemplary embodiments, flash edge 230 can also be disposed on the outside of the loop. More particularly, the inside, sides, and/or outside portions of the loop can be formed with a ridge 230 that extends around or along a portion thereof.

Figure 11:
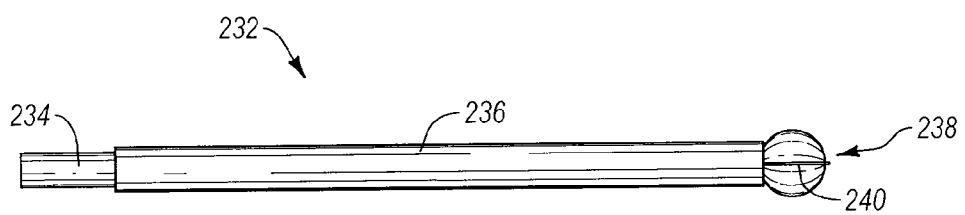
FIG. 11 illustrates a spherical electrode tip for use in cauterizing leaking blood vessels and sealing open structures, the spherical tip having a flash edge extending therearound.

FIG. 11 illustrates electrode tip 232, which is an electrode tip that may be used to specifically cauterize leaking blood vessels and to seal open structures. Electrode tip 232 includes connection end 234, sleeve fitting 236, and a spherical working end 238. As can be seen, a flash edge 240 extends around a circumference of spherical working end 238. In the illustrated embodiment, flash edge 240 extends around spherical working end 238 in a direction that is generally parallel to the length of electrode tip 232. As will be understood, flash edge 240 can extend in other directions, either partially or entirely around spherical working end 238. Additionally, flash edge 240 can also be disposed in locations on spherical working end 238 other than around a circumference of spherical working end 238.

As noted, some or all of the above-described electrode tips can include or be formed with one or more working surfaces having one or more flash edges. As also noted, these working surfaces and flash edges concentrate the electrical discharge from the electrode tip, thereby reducing the amount of extraneous charge loss in tissue which is not in close proximity to the working surface. The physical principles underlying the foregoing marked improvement can be understood with reference to FIGS. 12-14.

Figure 12:
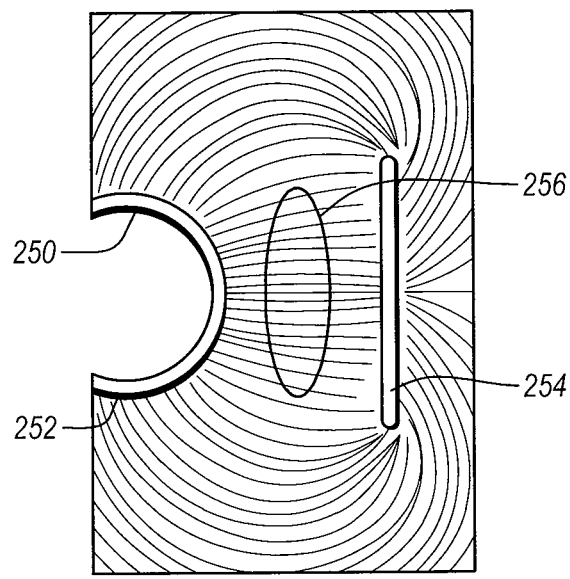
FIG. 12 is a schematic representation of a typical electric field existing between a rounded surface electrode tip and a working return electrode.

FIG. 12 is a diagram illustrating electric field pattern lines for an electric field existing between a conductor or electrode tip 250 having an annular, or curved, exterior surface 252 and a counter electrode 254. Although electrode 250 is shown in FIG. 12 as being hollow, the electric field pattern shown will be essentially the same if the electrode were solid. It will now be seen that the density of the electric field lines within ellipse 256 are nearly uniform and thus the electric field does not vary substantially within that region.

Figure 13:
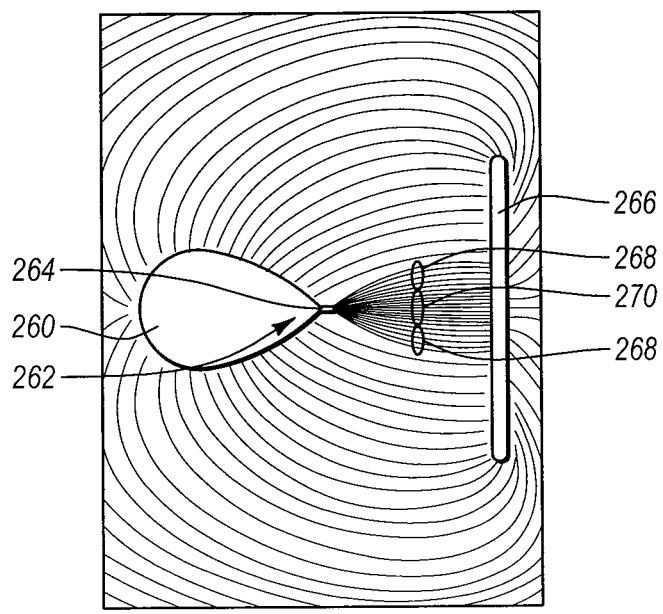
FIG. 13 is a schematic representation of a modified electric field concentration associated with an implement having a flash edge.

In FIG. 13, however, it will be noted that if the geometry of electrode 260 is made to include a tapered region 262 with a flash edge 264 extending therefrom, the corresponding electric field becomes much more concentrated as represented by the much greater line density of electric field lines near flash edge 264 between the electrode 260 and counter electrode 266. More particularly, tapered region 262 causes the density in the electric field resulting from tapered region 262 to become more concentrated, as can be seen from the greater line density within ellipses 268. Similarly, the narrow profile of the flash edge 264 causes an even greater concentration of the electric field, as can be seen from the even greater line density within ellipse 270.

Thus, on an irregularly shaped conductor, charge tends to accumulate at locations where the curvature of the surface is greatest, that is, along narrow surfaces such as flash edges, at sharp points, or edges. By including a flash edge on a working surface, the charge is concentrated along a much smaller surface area or region, thus focusing the electric field lines into a tighter arrangement. This tighter concentration of electric field lines focuses the energy and reduces the amount of energy needed to produce the desired electrosurgical effect, thereby reducing extraneous charge loss in tissue that is not in close proximity to the flash edge. The cutting surface or flash edge of the electrode need not be sharply pointed; it need only be shaped or sized to concentrate energy transfer to the degree desired for optimum cutting.

By way of illustration, a conventional unsharpened electrode has an edge thickness of about 0.33 mm and in a typical cutting mode may utilize a power setting nearing 50 watts. When tapered and having a flash edge thickness of about 0.0762 mm, a "sharpness" below that required of a mechanical scalpel blade, the electrodes of FIGS. 3-11 can quickly cut through tissue at less than 30 watts, a power setting of nearly 50% less than that required for a typical unsharpened electrode. Moreover, such blades cut more rapidly with less resistance, less eschar production, less thermal necrosis, and improved operator control.

Figure 14:
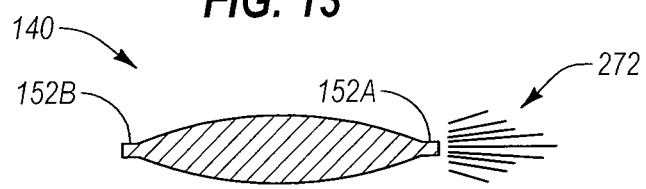
FIG. 14 is a simplified schematic representation of a typical concentration of electric field projected from the flash edge of FIG. 4A.

The foregoing principles are illustrated in FIG. 14. As noted above, FIG. 14 is a simplified view illustrating a typical concentration of electric field projected from electrode tip 140 illustrated in FIGS. 4 and 4A. As noted above, major surfaces 148A, 148B of electrode tip 140 taper toward one another and extend into flash edges 152A, 152B. To facilitate clarity and simplicity of presentation, only lines 272 representing the electric field in the direction of flash edge 152A are shown.

It will be observed that the electrode 140 of FIG. 14 is that earlier illustrated in FIG. 4A. Thus, there is shown electrically conductive main body 154 with tapered working surfaces 150A, 150B and flash edges 152A, 152B. When electrosurgical potential is applied to body 154 in the presence of tissue for which severance is desired, the density of energy transfer is concentrated at the end of flash edge 152A as represented by the longer rays within bundle of rays 272.

While electrode tips 140 and 260 illustrated in FIGS. 13 and 14 include both a tapered region and a flash edge, it will be understood and appreciated that an electrode tip according to the present invention does not need to have a tapered region. Rather, as illustrated in FIGS. 3 and 3A, an electrode tip according to the present invention can include a flash edge attached to or extending from a working surface that does not include a tapered region. Notwithstanding the absence of a tapered region, the flash edge will still concentrate the electric field as shown by ellipse 270 of FIG. 13. Thus, an electrode tip having a flash edge as described herein will significantly concentrate the electrical discharge from the electrode tip, thereby reducing the amount of extraneous charge loss in tissue which is not in close proximity to the working surface. In addition to limiting extraneous charge loss and associated tissue damage, tightly focusing or concentrating the electrical discharge improves the overall performance of the electrode tip, including the ease and speed of cutting.

Figure 15:
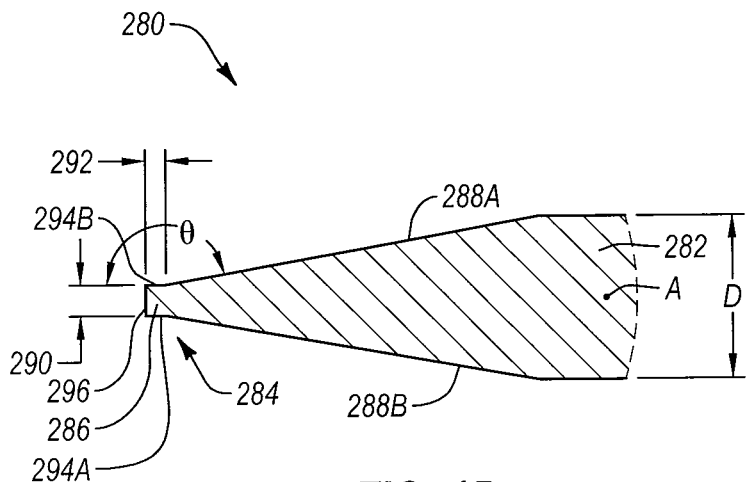
FIG. 15 is a cross-sectional view of a portion of an electrode tip having a flash edge according to an exemplary embodiment of the present invention.

It will be appreciated that electrode tip 140 is used by way of example, and the present discussion is applicable to the working surface(s) and flash edge(s) of each of the above-described electrode tips. It should also be understood that the dimensions of any flash edge are not limited to specific values. With reference to FIG. 15, the dimensions and associated considerations relating to a flash edge of an electrode tip will be discussed. It will be appreciated that the discussion of the flash edge illustrated in FIG. 15 is directly or generally applicable to any electrode tip that includes a flash edge. Thus, the specific configuration of the electrode tip illustrated and described in connection with FIG. 15 is not intended, and should not be considered, as limiting the scope of the present invention.

FIG. 15 illustrates a cross-sectional view of a portion of an electrode tip 280 having a main body 282 and a working surface 284. Similar to the electrode tips described above, working surface 284 includes or has extending therefrom a flash edge 286. In the illustrated embodiment, flash edge 286 has two opposing side surfaces 294A, 294B and face 296. While side surface 294A, 294B are illustrated as being generally flat and parallel to one another, it will be appreciated that side surfaces 294A, 294B can be rounded, tapered, or have other configurations. Similarly, while face 296 is illustrated as being a generally flat surface that is generally perpendicular to side surfaces 294A, 294B, it will be appreciated the face 296 may be rounded, tapered, sharpened, or have other configurations.

In the illustrated embodiment, main body 282 has two opposing major surfaces 288A, 288B that taper closer together as they approach flash edge 286. More specifically, major surfaces 288A, 288B are spaced apart a distance D near a central axis A of main body 282. As major surface 288A, 288B approach working surface 284, the distance therebetween narrows to a distance generally indicated by reference numeral 290. In one exemplary embodiment, distance D can range from between about 0.4064 mm to about 0.508 mm. In the illustrated embodiment, distance D is equal to about 0.4572 mm. As discussed below, distance 290 can range from between about 0.0125 mm and 0.125 mm. It will be understood that these values are exemplary only, and should not be construed as limiting the scope of the present invention.

Additionally, as noted above, major surfaces 288A, 288B can also be generally parallel to one another, similar to major surfaces 130A, 130B shown in FIGS. 3 and 3A. In such a situation, major surfaces 130A, 130B may not extend directly into the side surfaces of flash edges 134A, 134B. Additionally, the side surfaces of flash edges 134A, 134B may be generally parallel to major surfaces 130A, 130B, rather than forming a generally obtuse angle as described below. Likewise, a flash edge could also extend from an electrode tip having any other configuration and geometry, such as the electrode tips illustrated in FIGS. 4-11.

In the illustrated embodiment, two side surfaces 294A, 294B extend from two opposing surface 288A, 288B, respectively. As can be seen, major surface 288A and side surface 294A for an angle θ. Major surface 288B and side surface 294B similarly for an angle θ. Angle θ in the illustrated embodiment is equal to about 77°. It will be understood, in light of the disclosure herein, that angle θ can be equal to a variety of different angles based on the overall configuration of the electrode tip. For instance, angle θ can range anywhere from between about 90° to about 180°, depending on the configuration of the main body and the side surfaces of the flash edge.

Regardless of the general shape of main body 282 (i.e., tapered, squared, rounded, spherical, needle-like, etc.), or the relative orientation of the main body and the flash edge, many of the efficacious characteristics of the invention result from flash edge 286. As seen in FIG. 15, there are two dimensions of flash edge 286 that are considered when forming an electrode tip. The width 290 of flash edge 286 is principally responsible for producing the highly concentrated electric field described above in connection with FIGS. 12-14. As discussed above, the effectiveness of the electrode tip is affected by the concentration of the electric field. In addition, the concentration of the electric field also affects the amount of excess tissue damage surrounding an incision site. The more highly concentrated the electric field is the more effective the electrode tip is in cutting tissue without causing excessive tissue damage. The efficacious characteristics flowing from the invention begin to be significantly observed when the width 290 of the flash edge is generally between about 0.0125 mm and 0.125 mm, more preferably between about 0.0254 mm and 0.1016 mm, and most preferably about 0.0762 mm. In one exemplary embodiment, height 292 of the flash edge can extend up to about 6.5 mm. Nevertheless, from the disclosure herein, one of ordinary skill in the art will be able to readily determine various dimensional relationships for flash edge so as to achieve the desirable and advantageous performance characteristics described herein. Thus, the above-identified dimensional values are provided by way of non-limiting example. It will be appreciated that other dimensions and ranges may also be employed without departing from the scope of the present invention.

The width 290 and height 292 of flash edge 286 also provide advantageous characteristics to electrode tip 280 during the manufacturing and processing of electrode tip 280. Electrode tips as described herein can be formed using any suitable manufacturing process or technique. One such process that is particularly desirable because of its speed, simplicity, and cost effectiveness, is a stamping process. As is known to those skilled in the art, stamping is the process of forming and cutting a metal into a desired shape and size with the help of a stamping die loaded on a stamping press. Measurements have shown that when forming an electrode tip having a desired edge thickness, such as with a stamping process, the desired edge thickness is more readily achievable and more consistent when the desired thickness is formed as part of a flash edge. This is a result of many manufacturing processes that do not have extremely tight tolerance levels. For instance, when forming an electrode tip with a stamping process, the stamping die may be just slightly offset, thereby affecting the edge dimensions of the electrode tip. In contrast, when the desired edge dimension is formed in a flash edge, slight offsets in the stamping die may affect the height of the flash surfaces, but the thickness of the flash surfaces will remain unaffected.

During the manufacturing process, an electrode tip may go through several process steps, such as grinding, micro-machining, grit blasting, tumbling, polishing, and the like. One or more of these processes may wear away portions of the electrode tip's surfaces. By way of example, electrode blades with tapered or sharpened working surfaces are known in the art. These working surfaces are designed to concentrate the electrical discharge that is transferred to the patient's tissue. As these types of electrode tips, which do not include flash edges, are processed, the working surface may be worn away. The wearing away of this tapered or sharpened working surface may then reduce the effectiveness of the electrode tip. For instance, if enough of the tapered or sharpened working surface is sufficiently worn away, the resulting working surface may not be properly sized to effectively concentrate the electrical discharge. That is, as the tapered or sharpened working surface is worn down, the working surface becomes wider. As the working surface becomes wider, the electrical discharge that is transferred from the working surface becomes less concentrated. As discussed above, less concentrated electrical discharge results in less effective performance of the electrode tip and additional tissue damage surrounding the incision site.

In contrast, an electrode tip that includes a flash edge, such as electrode tip 280 of FIG. 15, is more resilient to such processing. As electrode tip 280, for example, goes through the various manufacturing processes (i.e., grinding, micro-machining, grit blasting, tumbling, polishing, and the like) some of the flash edge 286 may be worn away. Unlike a tapered or sharpened electrode tip without a flash edge, however, the amount of reduction in width 290 and/or height 292 of flash edge 286 caused by these processes will not likely be sufficient to substantially affect the performance of the electrode tip.

For instance, width 290 may be reduced from its initial dimension to a smaller or narrower dimension as a result of the abrasive manufacturing processes. Similar, these abrasive manufacturing processes may reduce height 292 from its initial dimension to a shorter dimension. Nevertheless, even if the dimensions of width 290 and/or height 292 of flash edge 286 were reduced during manufacturing, the resulting flash edge 286 could still present a working surface that has the thickness necessary to highly concentrate the electrical discharge as described above. That is, for example, if width 290 were reduced from an initial dimension of about 0.150 mm to about 0.1016 mm or about 0.0762 mm, width 290 would still be able to concentrate the electrical discharge that is transferred from the electrode tip to the patient sufficiently enough to produce the desirable performance attributes described herein. Likewise, if the dimension of height 292 were reduced by half, for example, the resulting flash edge would still be able to perform as described herein. Thus, the wearing away of some of the flash edge during the manufacturing processes will still allow the electrode tip to present a narrow working surface that concentrates the electrical discharge, rather that presenting a wider working surface that can result from the manufacturing processes performed on a tapered or sharpened electrode tip. Therefore, some of width 290 and/or height 292 of the flash edge can act as a sacrificial element that can be removed during the manufacturing processes without compromising or otherwise negatively impacting the performance characteristics associated with the electrode tip.

Figure 16:
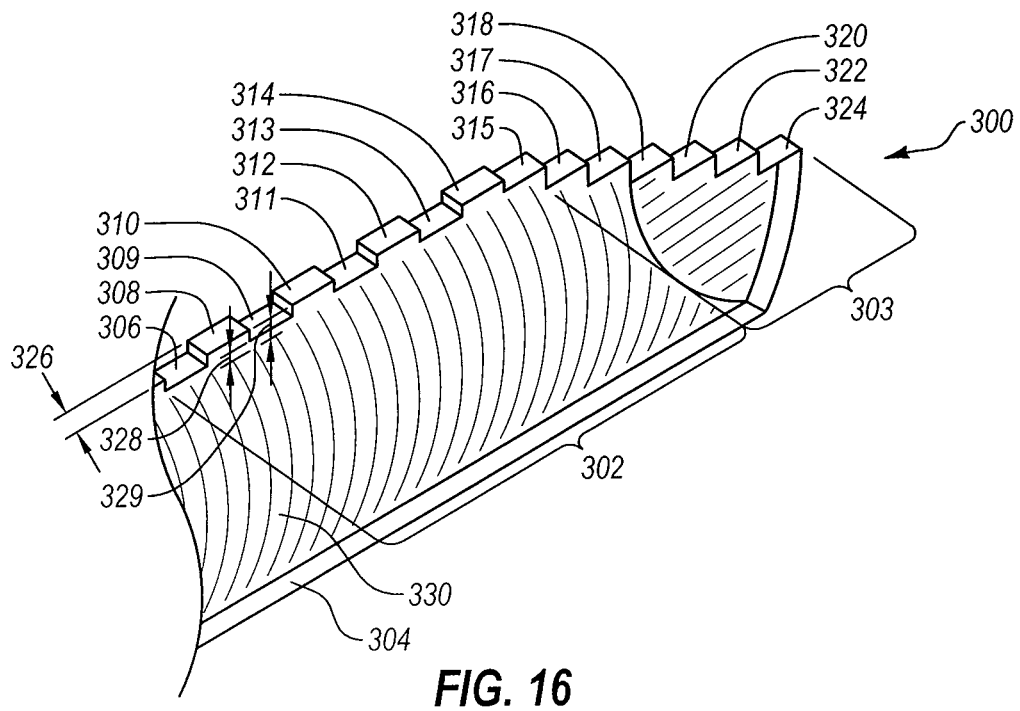
FIG. 16 is a perspective view of an exemplary electrode tip having three flash edge configurations, namely a uniform flash edge, an alternating height flash edge, and stepped flash edge, the alternating height and stepped flash edge functioning as a serrated flash edge.

Each of the novel electrode tips illustrated and described to this point have included a flash edge of generally uniform or constant dimensions along the working surface associated with the flash edge. Nevertheless, to enhance or alter the performance characteristics of an electrode tip, flash edges can be formed with dimensions that are non-uniform or change along the working surface. In FIG. 16, for example, there is illustrated an exemplary embodiment of a working end 300 of an electrode tip that has flash edges 302, 303, 304 which have differing configurations. Flash edge 304 is similar to the flash edges described above. Specifically, flash edge 304 extends along the length of one of the working surfaces of the electrode tip and has a generally constant or uniform width and height along the entire length of the electrode tip.

In contrast to flash edge 304, flash edges 302, 303 have multiple segments of different heights. Specifically, flash edge 302 includes segments 306, 308, 309, 310, 311, 312, 313, 314, 315 of alternating heights and flash edge 303 include segments 316, 317, 318, 320, 322, 324 which are arranged in a stepped configuration. The alternating heights or stepped configuration of the various segments of flash edges 303, 304 can result in unique performance characteristics. For instance, alternating the heights of the various segments or arranging the segments in a stepped configuration can produce a cutting effect that resembles a serrated blade.

With particular reference to flash edge 302 illustrated in FIG. 16, there can be seem multiple segments of different or alternating heights. Specifically, segments 306, 309, 311, 313, 315 have a height 328, and segments 308, 310, 312, 314 have a height 329. In the illustrated embodiment, height 329 is taller than height 328, thus providing the alternating heights for the various segments of flash edge 302. Alternating or varying the heights of the segments of flash edge 302 can provide a cutting effect that resembles the cutting effect of a serrated mechanical blade.

While segments 306, 309, 311, 313, 315 have been shown and described as each having a generally equal height 328, it will be appreciated that the height of each of segments 306, 309, 311, 313, 315 may not be same. For instance, each of segments 306, 309, 311, 313, 315 may have a different height from one another, or some segments may have generally the same height as other segments while some segments may have different heights than other segments. Likewise, segments 308, 310, 312, 314 may have generally the same heights or different heights as one another. Furthermore, while the lengths and widths 326 of each of segments 306, 308, 309, 310, 311, 312, 313, 314, 315 have been illustrated as being generally constant along flash edge 302, it will also be appreciated that segments 306, 308, 309, 310, 311, 312, 313, 314, 315 may have lengths and/or widths 326 that are the same or different from the other segments of flash edge 302.

The specific dimensions for width 326 and heights 328, 329 can be selected to provide desired performance characteristics. As described above, for example, width 326 can be generally between about 0.0125 mm and 0.125 mm, more preferably between about 0.0254 mm and 0.1016 mm, and most preferably about 0.0762 mm. Similarly, heights 328, 329 can be generally between about 0.0125 mm and about 6.5 mm. By way of non-limiting example, segments 306, 309, 311, 313, 315 may have a height of about 0.0125 mm while segments 308, 310, 312, 314 have a height of about 6.5 mm. In other words, a flash edge can be created in a discontinuous or alternating pattern to create or enhance the performance characteristics of the electrode tip.

With particular attention to flash edge 303 illustrated in FIG. 16, it can be seen that flash edge 303 includes multiple segments 316, 317, 318, 320, 322, 324. Similar to the segments of flash edge 302, each of segments 316, 317, 318, 320, 322, 324 is illustrated as having generally equal lengths and widths 326. As with the segments of flash edge 302, segments 316, 317, 318, 320, 322, 324 may also be configured with lengths and widths 326 that are different from one or more of the other segments of flash edge 303.

As shown in FIG. 16, segments 316, 317, 318, 320, 322, 324 of flash edge 303 are arranged in a stepped configuration. In other words, the face of each segment is vertically offset from or positioned lower than that the face of the immediately preceding segment. In particular, face of segment 316 is disposed at a first distance from the center of the electrode tip, while the face of segment 317 is disposed at a second distance from the center of the electrode tip that is shorter than the first distance. Similarly, each of the succeeding segments is disposed closer to the center of the electrode tip, thus providing the illustrated stepped configuration for flash edge 303. This stepped configuration can provide a cutting effect that resembles the cutting effect of a serrated mechanical blade As with the dimensions of segments of flash edge 302, the dimensions of segments 316, 317, 318, 320, 322, 324 can be selected to provide desired performance characteristics. For instance, the width of segments 316, 317, 318, 320, 322, 324 can be generally between about 0.0125 mm and 0.125 mm, more preferably between about 0.0254 mm and 0.1016 mm, and most preferably about 0.0762 mm. Similarly, the lengths and vertical offsets for each of segments 316, 317, 318, 320, 322, 324 can be selected for desired characteristics.

While many of the flash edges shown and described herein extend along an entire length of the associated working surface, it will be understood that other configurations are contemplated within the scope of the present invention. For instance, an electrode tip may have a single flash edge that extends along only a portion of one working surface. The single flash edge may take the form of any of the flash edges shown or described herein. For instance, a working surface may have a flash edge that is generally straight and uniform along the length of the working surface. Alternatively, the working surface may have a flash edge comprising segments of alternating heights, similar to flash edge 302. Still further, a working surface may have a flash edge having a stepped configuration, similar to flash edge 303.

Figure 17:
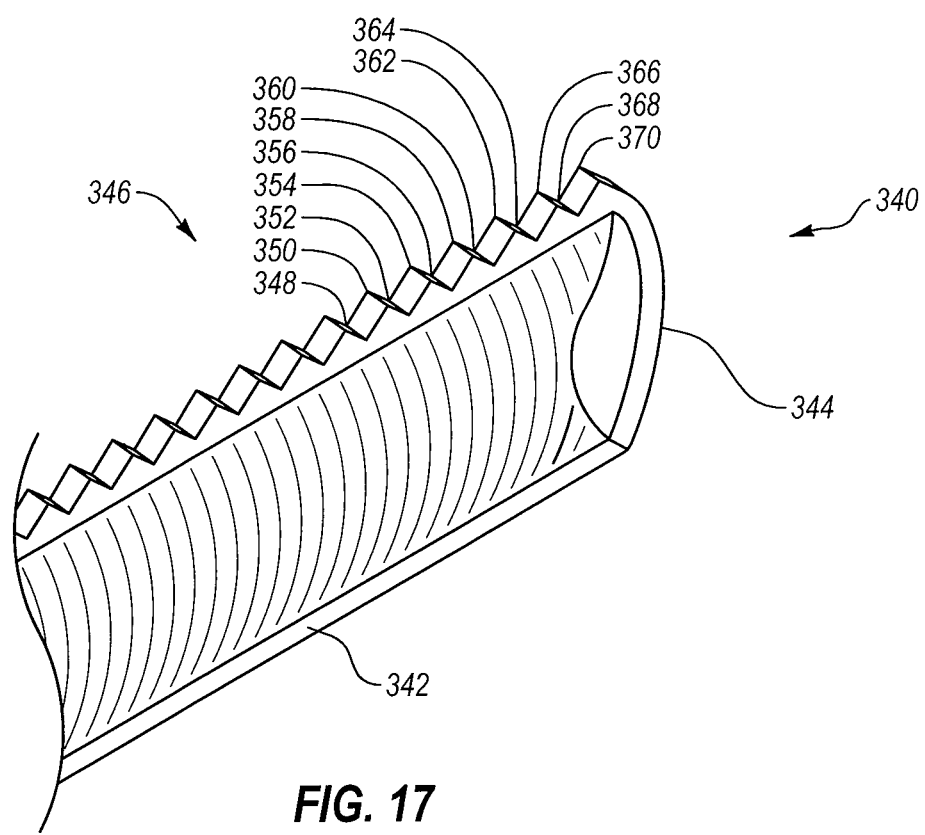
FIG. 17 is a perspective view of another exemplary electrode tip according to the present invention, the electrode tip having two flash edge configurations, namely a uniform flash edge and saw-tooth configured flash edge that functions as a serrated flash edge.

Attention is now directed to FIG. 17, which illustrates another exemplary electrode tip 340 having multiple flash edges. Similar to electrode tip 300 of FIG. 16, electrode tip 340 includes a flash edge 3340 which extends along the length of one of the working surfaces of the electrode tip and has a generally constant or uniform width and height along the entire length of the electrode tip. Electrode tip 340 also includes a flash edge 344 having generally constant or uniform width and height that extends along the end of electrode tip 340. The widths and heights of flash edges 342, 344 can be selected from the ranges described elsewhere herein.

Electrode tip 340 also includes a third flash edge 346 extending along the top working surface. Flash edge 346 is similar to flash edge 302 from FIG. 16 in that is includes multiple alternating segments 348, 350, 352, 354, 356, 358, 360, 362, 364, 366, 368, 370. Unlike flash edge 302 which includes squared segments, however, the segments of flash edge 346 are configured in a saw-tooth configuration. In other words, the segments of flash edge 346 form alternating peaks and valleys that are generally triangular in shape. Thus, for example, segments 348, 352, 356, 360, 364, 368 form triangular shaped valleys and segments 350, 354, 358, 362, 366, 370 form generally triangular peaks. The various peaks of flash edge 346 provided numerous points at which the electrical energy can be concentrated as it is transferred to patient tissue. In this manner, the segments of flash edge 346 provide serrated-type functionality to electrode tip 340. As with the other flash edges described herein, the heights, widths, and lengths of segments 348, 350, 352, 354, 356, 358, 360, 362, 364, 366, 368, 370 can be selected from the dimensional ranges described herein. Furthermore, the heights, widths, and lengths of segments 348, 350, 352, 354, 356, 358, 360, 362, 364, 366, 368, 370 can either be uniform or constant, or the various segments may have dimensions that are different from one or more of the other segments. Additionally, flash edge 346 can extend along all or a portion of a working surface of an electrode tip.

Electrode tips according to the present invention may have multiple flash edges disposed on multiple working surfaces, such as flash edges 302, 303, 304 illustrated in FIG. 16 or flash edges 342, 344, 346 of FIG. 17. Likewise, a single working surface of an electrode tip may have multiple flash edges or flash edge segments of different dimensions or configurations to provide enhanced or alternative performance characteristics, such as flash edges 302, 303 shown in FIG. 16 on the same side of working end 300. Thus, an electrode tip according to the present invention may have one or more working surfaces, each of which may have one or more flash edges or flash edge segments. In this manner, electrode tips can be formed so as to provide great versatility and variety in the number of different performance characteristics that can be achieved with a single electrode tip that includes a variety of different working surface/flash edge configurations.

Figure 18:
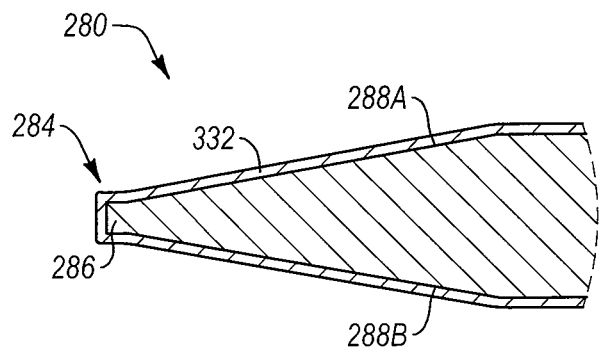
FIG. 18 is a view of an electrode tip similar to FIG. 15, with the electrode tip having a coating disposed on the outer surface thereof.
Figure 18A:
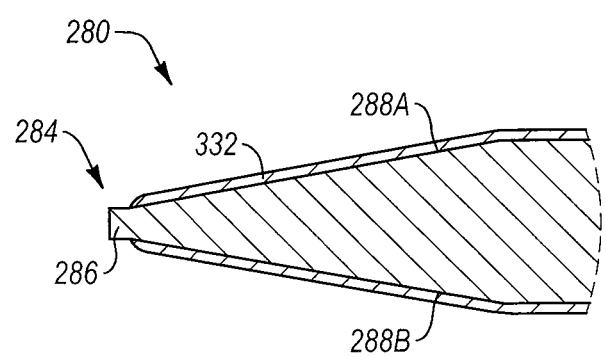
FIG. 18A is a view of an electrode tip similar to FIG. 17, with the electrode tip having a coating disposed on a portion of the outer surface thereof, while the flash edge is uncoated.

Attention is now directed to FIGS. 18 and 18A which illustrate electrode tip 280 (from FIG. 15) with a coating thereon. While electrode tip 280 is illustrated, it will be appreciated that the following discussion regarding coating an electrode tip is applicable to any electrode tip, including those described herein. With specific reference to FIG. 18, electrode tip 280 is shown with coating 332 disposed on the entire outer surface thereof. Coating 332 can provide one or more desirable attributes and/or properties at working surface 284. Such desirable properties and/or attributes can include a high temperature stability to withstand the temperatures of electrosurgery and a flexibility to increase the durability of the electrode tip. Additionally, a non-stick coating can serve to eliminate or reduce the clinging of charred tissue to the blade, thereby reducing incidences of unwanted tissue damage. A non-stick material suitable for use as a coating for electrode tips can be, but is not limited to, PTFE or a hybrid material that can include a combination of at least one of an organic material and an inorganic material, and that provides the coated surface with desirable properties, such as a high temperature stability, flexibility, and a low temperature application condition so that the coating layer may be applied by a spray or dip process. An example of a hybrid coating is provided in U.S. Pat. No. 6,951,559, entitled "Utilization of a Hybrid Material in a Surface Coating of an Electrosurgical Instrument" that issued on Oct. 4, 2005, to Greep, the disclosure of which is incorporated herein by reference in its entirety.

The thickness of the non-stick material can be sufficient such that transmission of radio frequency electrical energy from the coated electrode tip to the tissue of the patient can be essentially by capacitive coupling, ordinarily less than 0.025 mm. The precise optimum thickness will vary depending upon the material used and can be readily determined by routine experimentation. It will be evident that this coating mechanically "dulls" any sharp electrode edge, but as previously noted, cutting by electrosurgery does not necessarily require sharp surgical edges for mechanically severing tissue. Rather, the cutting is effected by utilizing sufficient energy to cause water in the tissue cells to boil and rupture the cell membranes.

While FIG. 18 illustrates the entire outer surface of electrode tip 280 being covered with coating 332, including major surfaces 288A, 288B and flash edge 286, it will be appreciated that coating 332 may only cover a portion of the outer surfaces of electrode tip 280. FIG. 18A illustrates electrode tip 280 partially coated with coating 332. In the illustrated embodiment, working surface 284/flash edge 286 are not covered by coating 332. In the embodiment of FIG. 18A, tissue severance is achieved principally by ohmic conduction of electrical energy from the exposed working surface 284/flash edge 286 to the tissue of the patient, rather than by transmission of electrical energy, via capacitive coupling, from a coated electrode tip to the tissue of the patient.

The coating configuration illustrated in FIG. 18A can be achieved in various ways. For instance, coating 332 can be applied to only a portion of electrode tip 280 (i.e., major surfaces 288A, 288B) while leaving working surface 284/flash edge 286 uncoated. Alternatively, coating 332 can be applied to the entire outer surface of electrode tip 280, including working surface 284/flash edge 286. After application to the entire outer surface of electrode tip 280, the portion of coating 332 that covers working surface 284/flash edge 286 can be removed. Coating 332 can be removed from the desired area(s) of electrode tip 280 is a variety of ways, including grit blasting, grinding, sanding, chemical removal processes, and the like. Additionally, the portion of coating 332 that covers working surface 284/flash edge 286 can be removed by activating and/or using electrode tip 280. The highly concentrated electrical discharge that is produced at flash edge 286 may be sufficient to cause the portion of coating 332 that covers working surface 284/flash edge 286 to evaporate, thereby exposing working surface 284/flash edge 286.

Leaving working surface 284/flash edge 286 uncoated or allowing coating 332 to evaporate off of working surface 284/flash edge 286 provides some advantageous characteristics to electrode tip 280. For instance, leaving or allowing flash edge 286 to become uncoated enables electrode tip 280 to achieve optimum energy concentration while preserving the insulation character of the remainder of the blade (i.e., major surfaces 288A, 288B). Additionally, because the electrical discharge is so highly concentrated along flash edge 286, the retention of coating 332 on the other surfaces of electrode tip (major surfaces 288A, 288B) is markedly improved. This improved coating retention increases the performance and longevity of the electrode tip.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrode tip adapted for use in performing electrosurgical operative procedures, the electrode tip comprising:
    a main body formed of a conductive material, the main body having a first major surface and a second major surface opposite the first major surface; and
    at least one working surface disposed on the main body, the at least one working surface comprising a flash edge extending from the main body, the flash edge having a first side surface and a second side surface opposite the first side surface, the first side surface and the first major surface forming an obtuse angle that opens away from the electrode tip, the flash edge being adapted to communicate electrical energy to patient tissue for performing electrosurgical operative procedures thereupon, wherein the flash edge is adapted to concentrate the electrical energy communicated to the patient tissue.

2. The electrode tip of claim 1, wherein the first major surface and the second major surface taper closer to one another adjacent the flash edge.

3. The electrode tip of claim 1, wherein the first major surface and the second major surface are generally parallel to one another.

4. The electrode tip of claim 1, wherein the flash edge has a face surface extending between the first side surface and the second side surface.

5. The electrode tip of claim 4, wherein the first side surface and the second side surface of the flash edge are substantially parallel to one another.

6. The electrode tip of claim 4, wherein the face surface is generally planar and is oriented generally perpendicular to the first side surface and the second side surface.

7. The electrode tip of claim 1, wherein the flash edge has a generally rectangular shaped cross-section.

8. The electrode tip of claim 1, wherein the flash edge has a width of between about 0.0125 mm and about 0.125 mm.

9. The electrode tip of claim 1, wherein the flash edge has a height of between about 0.0125 mm to about 6.5 mm.

10. The electrode tip of claim 9, wherein, through substantially the entire height of the flash edge, the flash edge has a generally uniform width.

11. The electrode tip of claim 1, wherein at least a portion of an outer surface of the main body has a coating applied thereto.

12. The electrode tip of claim 11, wherein the coating comprises a non-stick material.

13. The electrode tip of claim 11, wherein the portion of the outer surface of the main body that has the coating applied thereto comprises the first major surface and the second major surface of the main body.

14. An electrode tip adapted for use in performing electrosurgical operative procedures, the electrode tip comprising:
    a main body, formed of a conductive material, adapted to be electrically connected to an electrosurgical generator to facilitate communication of electrical energy from the electrosurgical generator to the electrode tip, the main body having two opposing major surfaces and a working surface, the working surface comprising a flash edge that extends from the main body, the flash edge having a generally rectangular shaped cross-section, the flash edge being adapted to communicate the electrical energy from the main body to patient tissue for performing electrosurgical operative procedures thereupon, the flash edge having two opposing side surfaces and a face surface, the two opposing side surfaces of flash edge being spaced apart from one another by a distance of between about 0.0125 mm and about 0.125 mm to concentrate the electrical energy communicated to the patient tissue.

15. The electrode tip of claim 14, wherein at least one of the major surfaces of the main body forms an angle of between about 90° to less than about 180° with at least one of the side surfaces of the flash edge.

16. The electrode tip of claim 15, wherein the angle formed between the at least one of the major surfaces of the main body and the at least one of the side surfaces of the flash edge opens away from the electrode tip.

17. The electrode tip of claim 14, wherein the two opposing side surfaces of flash edge are spaced apart from one another by a distance of between about 0.0254 mm and about 0.1016 mm.

18. The electrode tip of claim 14, wherein the main body is generally in the form of a scalpel-type electrode tip, an L-hook electrode tip, a J-hook electrode tip, a loop-type electrode tip, a needle electrode tip, or a ball electrode tip.

19. The electrode tip of claim 14, wherein the two opposing major surfaces of the main body taper closer to one another as the two opposing major surfaces approach the working surface.

20. An electrode tip adapted for use in performing electrosurgical operative procedures, the electrode tip comprising:
    a connection end adapted to be electrically connected to an electrosurgical generator to facilitate communication of electrical energy from the electrosurgical generator to the electrode tip;
    a main body, formed of a conductive material, operatively associated with the connection end, the main body having two opposing major surfaces and a working surface, the two opposing major surfaces being spaced apart a first distance near a central axis of the main body, the two opposing major surfaces being spaced apart a second, smaller distance near the working surface, the working surface comprising a flash edge adapted to communicate the electrical energy from the main body to patient tissue for performing electrosurgical operative procedures thereupon, the flash edge having two opposing side surfaces and a face surface, at least one of the two opposing side surfaces of the flash edge extending from at least one of the two opposing major surfaces of the main body at an angle of between about 90° and less than about 180°, the angle opening away from the main body, the two opposing side surfaces of the flash edge being spaced apart a distance of between about 0.0125 mm and about 0.125 mm to concentrate the electrical energy communicated to the patient tissue.

21. The electrode tip of claim 20, wherein the flash edge has a generally rectangular shaped cross-section.

22. The electrode tip of claim 20, wherein the two opposing side surfaces of the flash edge are space apart by a distance of about 0.0762 mm.

23. The electrode tip of claim 20, wherein the main body is coated with a non-stick material.

24. The electrode tip of claim 20, wherein the flash edge extends from the main body by a distance of between about 0.0125 mm to about 6.5 mm.

25. The electrode tip of claim 20, wherein at least a portion of the flash edge comprises a sacrificial element that can be removed while maintaining the electrical energy concentrating capabilities of the flash edge.

\* \* \* \* \*